United States Patent [19]

VanderSloot

[11] Patent Number: 5,096,709
[45] Date of Patent: Mar. 17, 1992

[54] MUSCLE RELAXANT AND ANALGESIC CONTAINING OIL OF MELALEUCA, SPP.

[75] Inventor: Frank L. VanderSloot, Idaho Falls, Id.

[73] Assignee: Melaleuca, Inc., Idaho Falls, Id.

[21] Appl. No.: 449,238

[22] Filed: Dec. 7, 1989

Related U.S. Application Data

[63] Continuation of Ser. No. 191,266, May 9, 1988, abandoned.

[51] Int. Cl.$^5$ ............................................. A61K 35/78
[52] U.S. Cl. .................................. 424/195.1; 514/906
[58] Field of Search ...................... 424/195.1; 514/906

[56] References Cited

FOREIGN PATENT DOCUMENTS 74968  4/1981  Australia .
559001 2/1987  Australia .
126421 3/1966  Czechoslovakia .

OTHER PUBLICATIONS

*Handbook of Nonprescription Drugs,* published by The National Professional Society of Pharmacists, 5th edition, pp. 289-295.

*Melaleuca Alternifolia,* by Essential Oils Data Search, Inc. copyright 1985, pp. 15, 19-23, 30-36, 42-49, 51-57 and 62-88.

*Primary Examiner*—Lester L. Lee
*Assistant Examiner*—S. G. Marshall
*Attorney, Agent, or Firm*—Workman, Nydegger & Jensen

[57] ABSTRACT

A muscle relaxant and analgesic composition having at least five percent and preferably ten percent oil of Melaleuca spp. therein. The composition also contains other aromatic oils, such as camphor, menthol and methyl salicylate, a thickening agent, a preservative, and a carrier. The composition provides relief for sore muscles or joints when applied topically to the affected area. The Melaleuca oil preferably contains at least thirty percent terpinen-4-ol and less than fifteen percent 1,8-cineole.

10 Claims, No Drawings

MUSCLE RELAXANT AND ANALGESIC CONTAINING OIL OF MELALEUCA, SPP.

CROSS-REFERENCE TO RELATED APPLICATIONS

This is a continuation of application Ser. No. 07/191,266, filed 05/09/88, now abandoned.

BACKGROUND OF THE INVENTION

The present invention relates to the use of melaleuca oil as a muscle relaxant and analgesic, in combination with other ingredients to produce a penetrating, long-lasting cream for topical application. In particular, the invention relates to the manufacture of a muscle relaxant containing at least five percent, and preferably ten percent, melaleuca oil. The oils of Melaleuca spp. have been used for a number of years as a bactericide and fungicide topically applied to wounds, abrasions, etc. The germicidal nature of melaleuca oil has been known since at least 1930, when it was reported that the oil had a Rideal-Walker co-efficient of 11-13, meaning it has 11-13 times the efficacy of phenol as a germicide. The oil of Melaleuca is distilled from the leaves and terminal branchlets of various Melaleuca species indigenous to the north coast of New South Wales, Australia. Such oil can contain up to fifteen percent 1-8 cineole and a minimum of thirty percent terpinen-4-ol, on a weight/weight basis.

While the existing literature on the uses of melaleuca oil is mostly in anecdotal format, it appears that the oil has never gained wide-spread acceptance as a fungicide even though it has been periodically used for a large number of bactericidal or fungicidal purposes. While the medical use of melaleuca oil reached its peak in the mid-twentieth century, its use since that time has steadily declined. Surprisingly, it would appear that the use of melaleuca oil as a muscle relaxant, when used in an appropriate mixture with other ingredients, has heretofore gone undiscovered.

Melaleuca oil is a complex mixture of approximately forty-eight separate compounds. While it is not known precisely why the oil produces the analgesic and therapeutic affects observed in the present invention and in its germicidal properties, it is believed that the concentration of terpinen-4-ol may be a major factor. At the same time, the low concentration of another major constituent (1,8-cineole) is advantageous due to its known propensity for skin irritation.

Therefore, applicant's discovery of this new use of a mixture containing at least five percent, and preferably ten percent melaleuca oil, is surprising in that it produces the desired affect where many other products fail. While analgesic balms have been known for some time and are currently mass-marketed for the relief of local muscle and joint discomfort, such products are limited effectiveness and have relatively short duration, and require relatively frequent reapplication. There is therefore a need for an effective analgesic and muscle relaxant which is penetrating, long-acting, effective and which produces no adverse skin reaction.

SUMMARY OF THE INVENTION

The present invention comprises a mixture of various aromatic oils, including melaleuca oil, with a thickening agent, a preservative and a carrier, so that the resulting cream may be easily applied to a localized area of muscle strain or soreness. The mixture comprises at least five percent, and preferably ten percent by weight, of melaleuca oil having at least thirty percent by weight, terpinen-4-ol and less than fifteen percent by weight, 1,8-cineole therein. In addition to melaleuca oil one or more of the oils selected from the group of camphor, menthol and methyl salicylate may additionally be used. Preservatives to prevent microbial growth and a thickening agent to produce a cream-like consistency are also added. Depending upon the order of addition of the ingredients, the carrier may be either or both of isopropyl alcohol and/or water.

While melaleuca oil is useable topically in an undiluted form, such use does not provide the benefits of the present invention. The synergistic effect of the combination of ingredients set forth herein, as well as the relatively high cost of melaleuca oil indicate that its use as a muscle relaxant in the form set forth herein is preferred.

DETAILED DESCRIPTION OF THE INVENTION

The analgesic and muscle relaxant composition of the present invention comprises a mixture of a number of aromatic oils, including melaleuca oil, camphor, menthol and methylsalicylate. Melaleuca oil, derived from the steam distillation of Melaleuca spp., has been well known as a bactericide and fungicide, but whose properties as a muscle relaxant have been newly discovered by the applicant. It is believed that oil of Melaleuca is a "penetrating" oil to some degree, as evidenced by the ability to penetrate blisters or pustules and heal the underlying damaged skin, as well as the fact that pure melaleuca oil stored in plastic containers will migrate through the interstices of the container without affecting the container.

The unique combination of the aromatic oils of the present invention greatly enhance the analgesic properties of the other ingredients in the mixture. Methyl salicylate (or winter-green oil) is derived by heating methanol and salicylic acid in the presence of sulfuric acid, or by distillation of leaves of *Gaultheria procumbuns* or the bark of *Betula lenta*. It has variously been used as an analgesic which "heats" skin upon which it is topically applied. Menthol (or peppermint camphor) is derived from peppermint oil by freezing or can be synthesized from *Citronellal thymol* or turpentine oil. It is generally known to be a moderate irritant to certain mucous membranes and has been used in cough drops, chest rubs, etc. Camphor (a ketone occurring naturally in the wood of the camphor tree) is obtained by steam distillation of camphor tree wood or may be synthesized from pinene or turpentine oil. While melaleuca oil has heretofore been used primarily as a bactericide and fungicide, applicant has discovered that it exhibits certain "numbing" properties when applied topically to the skin in the mixture set forth herein.

While it is believed that melaleuca oil will exhibit certain analgesic and muscle relaxant properties when applied topically in a pure form, it is not believed that significantly improved results are obtained when so applied, as contrasted to the mixture of the present invention. Not only is the expense many times greater when applied in a pure form, but there appear to be certain synergistic affects when melaleuca oil is applied in combination with the other aromatic oils as disclosed herein. Therefore, applicant has determined that at least five percent, and preferably ten percent by weight, melaleuca oil when applied topically to sore joints or injured muscles in the cream form of the present invention, results in a pleasing and soothing relaxation of the affected area. While the combination of aromatic oils could simply be diluted in a liquid carrier and rubbed into the skin as a liquid, applicant has chosen to suspend the various oils in a cream-like suspension to insure that the oils remain uniformly in suspension and can thereafter be uniformly applied to the affected area.

In the preferred embodiment, it is preferable to add some sort of preservative to the suspension to prevent microbial growth which might adversely affect the efficacy of the product as well as its appearance. For that purpose, applicant has chosen methylparaben and propylparaben, which, when added in relatively small amounts prevents any spoilage due to microbial growth.

In order to effectively emulsify the various components of the mixture, a surfactant must be added to the mixture. Applicant has found that polysorbate (a polyoxyethylene derivative obtained by esterification of a sorbital with a fatty acid) is particularly useful. In order to suspend the active ingredients in a thick suspension, a thickening agent must be added. While any thickening agent known to those of ordinary skill in the art may be utilized, applicant has determined that tragacanth gum (occurring naturally in southwest Europe and the Middle East) is particularly useful for this purpose.

The principles of the present invention are evident in the following example:

EXAMPLE

The ingredients set forth below:

| Ingredient | Percent W/W |
|---|---|
| Water | 58.5 |
| Isopropyl alcohol | 13.2 |
| Methylsalicylate | 10.0 |
| Melaleuca Oil | 10.0 |
| Polysorbate | 2.0 |
| Methylparaben | 1.79 |
| Propylparaben | 1.79 |
| Tragacanth Gum | 1.60 |
| Menthol | 0.50 |
| Camphor | 0.50 |
| Color | 0.816, Green |
| | 0.292, Blue #1 | were combined as follows:

The menthol and camphor oils were dissolved in a portion of the isopropyl alcohol, resulting in a completely mixed solution. The remainder of the alcohol was added to the water and stirred. The tragacanth gum, methylparaben and propylparaben were added to a high-speed mixer and the remainder of the alcohol/water mixture was added thereto. This solution was stirred vigorously until a relatively uniform suspension was formed. To this suspension was added the polysorbate, the melaleuca oil, and the menthol/camphor solution. This suspension was further stirred until totally disbursed. This solution was then transferred to a blender and thoroughly mixed. The colors were added, at which point a hand-cream consistency mixture having a pleasing aqua color was produced.

When applied topically to sore muscles, arthritic joints, canker sores, bee stings, sunburn and other minor pains, the product penetrates the skin and produces an immediate soothing of the affected area. The product must be stored and sold in glass containers, as the melaleuca oil therein has been known to penetrate plastic containers.

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

I claim:

1. A muscle relaxant and analgesic composition comprising, by weight: from 5 percent to about 10 percent melaleuca oil extracted from Melaleuca spp., 0.5 percent camphor; 0.5 menthol; 10 percent methyl salicylate; 1.6 percent tragacanth gum; 1.79 percent propylparaben; 1.79 percent methylparaben; 2 percent of a surfactant; and a carrier mixture comprising alcohol and water.

2. A method for relaxing muscles and for providing topical analgesia comprising the steps of:
   (a) obtaining a muscle relaxant and analgesic composition comprising by weight: from 5 percent to about 10 percent melaleuca oil extracted from Melaleuca spp., 0.5 percent camphor; 0.5 percent menthol; 10 percent methyl salicylate; 1.6 percent tragacanth gum; 1.79 percent propylparaben; 1.79 percent methylparaben; 2 percent of a surfactant; and a carrier mixture comprising alcohol and water; and
   (b) topically applying an effective amount of the composition to the intended area to allow penetration of the composition, thereby relaxing muscles and providing a topical analgesia.

3. A muscle relaxant and analgesic composition as set forth in claim 1, wherein said melaleuca oil is extracted from *Melaleuca alternifolia*.

4. A muscle relaxant and analgesic composition as set forth in claim 1, wherein said melaleuca oil contains at least 30 percent terpinen-4-ol.

5. A muscle relaxant and analgesic composition as set forth in claim 1, wherein said melaleuca oil contains less than 15 percent, 1,8-cineole.

6. A muscle relaxant and analgesic composition as set forth in claim 5, wherein said melaleuca oil contains at least 30 percent terpinen-4-ol.

7. A method for relaxing muscles and for providing topical analgesia as set forth in claim 2, wherein said melaleuca oil is extracted from *Melaleuca alternifolia*.

8. A method for relaxing muscles and for providing topical analgesia as set forth in claim 2, wherein said melaleuca oil contains less than 15 percent 1,8-cineole.

9. A method for relaxing muscles and for providing topical analgesia as set forth in claim 2, wherein said melaleuca oil contains at least 30 percent terpinen-4-ol.

10. A method for relaxing muscles and for providing topical analgesia as set forth in claim 9, wherein said melaleuca oil contains less than 15 percent 1,8-cineole.

* * * * *

UNITED STATES PATENT AND TRADEMARK OFFICE
CERTIFICATE OF CORRECTION

PATENT NO.    : 5,096,709
DATED         : March 17, 1992
INVENTOR(S)   : FRANK L. VANDERSLOOT It is certified that error appears in the above-identified patent and that said Letters Patent is hereby corrected as shown below:

Column 1, line 53, "affect" should be --effect--

Column 1, line 56, "are" should be --have--

Signed and Sealed this

Twenty-eighth Day of September, 1993

*Attest:*

BRUCE LEHMAN

*Attesting Officer*    *Commissioner of Patents and Trademarks*